US008062383B2

(12) United States Patent
Tateishi

(10) Patent No.: US 8,062,383 B2
(45) Date of Patent: Nov. 22, 2011

(54) AZO PIGMENT COMPOSITION, PROCESS FOR PRODUCING AZO PIGMENT COMPOSITION, DISPERSION CONTAINING AZO PIGMENT COMPOSITION, COLORING COMPOSITION AND INK FOR INKJET RECORDING

(75) Inventor: Keiichi Tateishi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/921,277

(22) PCT Filed: Mar. 5, 2009

(86) PCT No.: PCT/JP2009/054181
§ 371 (c)(1),
(2), (4) Date: Sep. 7, 2010

(87) PCT Pub. No.: WO2009/110558
PCT Pub. Date: Sep. 11, 2009

(65) Prior Publication Data
US 2011/0023753 A1    Feb. 3, 2011

(30) Foreign Application Priority Data

Mar. 7, 2008  (JP) ................ 2008-058711
Jun. 27, 2008 (JP) ................ 2008-169182
Dec. 9, 2008  (JP) ................ 2008-313754

(51) Int. Cl.
C09B 67/00    (2006.01)
C09D 11/00    (2006.01)
(52) U.S. Cl. .......... 8/637.1; 8/639; 8/662; 8/688; 8/690; 8/692; 8/693; 106/31.13
(58) Field of Classification Search .............. 8/637.1, 8/639, 662, 688, 690, 692, 693; 106/31.13
See application file for complete search history.

(56) References Cited

U.S. PATENT DOCUMENTS
2,936,306 A    5/1960    Shmid et al.
(Continued)

FOREIGN PATENT DOCUMENTS
EP    01847570 A1    10/2007
(Continued)

OTHER PUBLICATIONS
STIC Search Report dated Sep. 10, 2011.*
(Continued)

Primary Examiner — Eisa Elhilo
(74) Attorney, Agent, or Firm — Sughrue Mion, PLLC

(57) ABSTRACT

To provide an azo pigment composition having extremely good hue and extremely good light fastness and showing excellent tinctorial strength (color density) and, preferably, to provide an azo pigment composition further containing an azo pigment having characteristic X-ray diffraction peaks at different positions or a tautomer thereof An azo pigment composition which contains at least one azo pigment represented by the following formula (1) and having characteristic peaks at Bragg angles (2θ±0.2°) of 7.2° and 25.9° in X-ray diffraction with the characteristic Cu Kα line, or a tautomer thereof:

(1):

11 Claims, 2 Drawing Sheets

U.S. PATENT DOCUMENTS

| | | |
|---|---|---|
| 4,282,144 A | 8/1981 | Weaver et al. |
| 4,579,949 A | 4/1986 | Rochat et al. |
| 4,870,164 A | 9/1989 | Kuhne et al. |
| 5,194,088 A | 3/1993 | Babler et al. |
| 2006/0107868 A1 | 5/2006 | Potenza et al. |
| 2008/0058531 A1 | 3/2008 | Schmidt et al. |

FOREIGN PATENT DOCUMENTS

| | | |
|---|---|---|
| JP | 55-161856 A | 12/1980 |
| JP | 56-38354 A | 4/1981 |
| JP | 58-210084 A | 12/1983 |
| JP | 5-222314 A | 8/1993 |
| JP | 8-48908 A | 2/1996 |
| JP | 11-100519 A | 4/1999 |
| JP | 2002-371214 A | 12/2002 |
| JP | 2003-246942 A | 9/2003 |
| JP | 2003-277662 A | 10/2003 |
| JP | 2004-137487 A | 5/2004 |
| JP | 2005-213357 A | 8/2005 |
| JP | 2006-57076 A | 3/2006 |
| JP | 2007-63520 A | 3/2007 |
| JP | 2007-217681 A | 8/2007 |
| JP | 2007-302810 A | 11/2007 |
| WO | 2006/055466 A1 | 5/2006 |
| WO | 2006/119846 A2 | 11/2006 |

OTHER PUBLICATIONS

English Abstract of the Japanese Patent # JP 2007302810 A ( Nov. 2007).*

International Search Report [PCT/ISA/210] dated Apr. 28, 2009 for PCT/JP2009/054181.

Written Opinion [PCT/ISA/237] dated Apr. 28, 2009 for PCT/JP2009/054181.

European Search Report for European Patent Application No. 09717226.6 dated Jun. 29, 2011.

* cited by examiner

AZO PIGMENT COMPOSITION, PROCESS FOR PRODUCING AZO PIGMENT COMPOSITION, DISPERSION CONTAINING AZO PIGMENT COMPOSITION, COLORING COMPOSITION AND INK FOR INKJET RECORDING

TECHNICAL FIELD

The present invention relates to an azo pigment composition, a process for producing an azo pigment composition, a dispersion containing an azo pigment composition, a coloring composition and an ink for inkjet recording.

BACKGROUND ART

In recent years, as image-recording materials, materials for forming color images have been particularly predominant and, specifically, recording materials for an inkjet system, recording materials for a thermal transfer system, recording materials for an electrophotographic system, transfer type silver halide light-sensitive materials, printing inks, and recording pens have found widespread use. Also, in photographing devices such as CCDs for photographing equipment, and in LCDs and PDPs for display, color filters are used for recording or reproducing a color image. In these color image recording materials and color filters, colorants (dyes or pigments) of three primary colors of a so-called additive color mixing process or subtractive color mixing process have been used in order to display or record full-color images. In actuality, however, there is no fast colorant having the absorption characteristics capable of realizing a preferred color reproduction region and resisting various use conditions and environmental conditions. Thus, the improvement thereof has strongly been desired.

Dyes or pigments to be used for the above-mentioned uses are required to have in common the following properties. That is, they are required to have absorption characteristics favorable in view of color reproduction and have good fastness under the conditions of the environment wherein they are used, for example, fastness against light, heat, and an oxidative gas such as ozone. In addition, in the case where the colorant is a pigment, the pigment is further required to be substantially insoluble in water or in an organic solvent, to have a good fastness to chemicals, and not to lose the preferred absorption characteristics it shows in a molecularly dispersed state even when used as particles. Although the required properties described above can be controlled by adjusting the intensity of intermolecular mutual action, both of them are in a trade-off relation with each other, thus being difficult to allow them to, be compatible with each other.

Besides, in the case of using a pigment as the colorant, the pigment is additionally required to have a particle size and a particle shape necessary for realizing desired transparency, to have good fastness under the conditions of the environment wherein they are used, for example, fastness against light, heat, and an oxidative gas such as ozone, to have good fastness to an organic solvent and chemicals such as a sulfurous acid gas, and to be capable of being dispersed in a used medium to a level of fine particles, with the dispersed state being stable. In particular, those pigments have been strongly desired which have a good hue, show a high tinctorial strength in light, heat and moisture and in an active gas present in the environment, and is fast against light.

That is, in comparison with a dye which is required to have properties as dye molecules, the pigment is required to have more properties, i.e., it is required to satisfy all of the above-mentioned requirements as a solid of an aggregate of a colorant (dispersion of fine particles) as well as the properties as molecules of a coloring material. As a result, a group of compounds which can be used as pigments are extremely limited, in comparison with dyes. Even when high-performance dyes are converted to pigments, few of them can satisfy requirement for the properties as a dispersion of fine particles. Thus, such pigments are difficult to develop. This can be confirmed from the fact that the number of pigments registered in Color Index is no more than 1/10 of the number of dyes.

Azo pigments are excellent in hue and tinctorial strength which are characteristics of coloring, and hence they have widely been used in printing inks, inks for an inkjet system, and electrophotographic materials. Of the pigments, the most typically used azo pigments are yellow diarylide pigments and red naphthol azo pigments. Examples of such diarylide pigments include C.I. pigment yellow 12, C.I. pigment yellow 13, and C.I. pigment yellow 17. Examples of the naphthol azo pigments include C.I. pigment 208 and C.I. pigment 242. However, these pigments are inferior in fastness, particularly light fastness, and hence they are decomposed when prints printed by them are exposed to light, thus being inappropriate for prints which are to be stored for a long time.

In order to remove such defects, there have been disclosed azo pigments having a fastness improved by increasing molecular weight or by introducing a group having a strong intermolecular mutual action (see, for example, patent documents 1 to 3). However, even the improved pigments, for example, the pigments described in patent document 1 have the defect that they have still insufficient light fastness though improved to some extent, and pigments described in, for example, patent documents 2 and 3 have a greenish hue and a low tinctorial strength, thus being inferior in coloring characteristics.

Also, patent documents 4 and 5 disclose colorants which have absorption characteristics of excellent color reproducibility and have a sufficient fastness. However, all of the specific compounds described in the patent documents are soluble in water or in an organic solvent, thus being insufficient in fastness to chemicals.

In the case of expressing a full-color image based on the subtractive color mixing process using three colors of yellow, magenta, and cyan or using four colors further including black, use of a pigment having an inferior fastness as a one color pigment, gray balance of the prints would be changed with the lapse of time, and use of a pigment having inferior coloring characteristics would reduce color reproducibility upon printing. Thus, in order to obtain prints which can maintain high color reproducibility for a long time, there have been desired a pigment and a pigment dispersion which have both good coloring characteristics and good fastness.

Azo colorants have conventionally been utilized as colorants in various fields since they often have various visible light absorptions. For example, they have come into use in various fields such as coloration of synthetic resins, printing inks, colorants for sublimation type thermal transfer materials, inks for inkjet recording, and colorants for color filters. Major performances required for azo colorants as colorants include an absorption spectrum. Hue of a colorant exerts a great influence on color tone and feeling of a body colored with the colorant, giving a large effect on visual sensation. Therefore, there have long been made studies on absorption spectrum of a colorant.

Conventionally known azo dyes containing a nitrogen-containing, 5-membered ring as an azo component are also disclosed in patent documents 6 and On the other hand, many of typical organic pigments are polymorphic and, in spite of having the same chemical formulation, such pigments are known to take two or more crystal forms.

Of organic pigments, some organic pigments such as azo pigments can form fine and size distribution-controlled particles by selecting appropriate reaction conditions upon synthesis thereof, and there are pigments such as copper phthalocyanine green which are formed into pigments by allowing extremely fine and aggregated particles produced upon synthesis to grow in a subsequent step with size distribution being controlled, and pigments such as copper phthalocyanine blue pigment which are formed into pigments by pulverizing coarse and uneven particles produced upon synthesis in a subsequent step and controlling the size distribution. For example, a diketopyrrolopyrrole pigment is generally synthesized by reacting a succinic diester with an aromatic nitrite in an organic solvent (see, for example, patent document 8). The crude diketopyrrolopyrrole pigment is heat-treated in water or in an organic solvent, and then subjected to pulverization such as wet milling into a form appropriate for use (see, for example, patent document 9). For example, with a diketopyrrolopyrrole pigment of C.I. Pigment Red 254, an α-type crystal form and a β-type crystal form are known (see, for example, patent document 10). Also, with an azo pigment of C.I. Pigment Yellow 181, several crystal forms are known (see, for example, patent document 11).

Patent document 1: JP-A-56-38354
Patent document 2: U.S. Pat. No. 2,936,306
Patent document 3: JP-A-11-100519
Patent document 4: JP-A-2005-213357
Patent document 5: JP-A-2003-246942
Patent document 6: JP-A-55-161856
Patent document 7: JP-A-2002-371214
Patent document 8: JP-A-58-210084
Patent document 9: JP-A-5-222314
Patent document 10: JP-A-8-48908
Patent document 11: US Patent Application Publication No. 2008/058531

DISCLOSURE OF THE INVENTION

Problems that the Invention is to Solve

The present invention relates to an azo pigment composition containing an azo pigment of a crystal form of bisazo pigment wherein two parent nuclei of the colorant each constituted by a specific substituent-having pyrazole ring, an azo group, and another pyrazole ring having a different substituent are linked to each other through a triazine ring, or a tautomer thereof, with the excellent stability and production process thereof not having been known so far.

Further, an object of the invention is to provide a coloring composition containing the azo pigment composition.

Also, another object of the invention is to provide a process for producing the azo pigment composition, which enables production of the composition with good reproducibility and high efficiency while controlling structural isomerization and crystal polymorphism.

A further object of the invention is to provide a coloring composition containing the dispersion of the azo pigment composition and provide an ink for inkjet recording containing the dispersion.

Means for Solving the Problem

As a result of intensive investigations in consideration of the above-mentioned circumstances, the inventors have found that an azo pigment composition containing an azo pigment having characteristic X ray diffraction peaks at specific positions or a tautomer thereof shows extremely good dispersibility and dispersion stability and has excellent hue and tinctorial strength. Further, the inventors have found a process for producing an azo pigment composition with good reproducibility and high efficiency while controlling so as to obtain specific structural isomerization and crystal polymorphism, thus having completed the invention.

That is, the invention is as follows.

(1). An azo pigment composition comprising at least one azo pigment represented by the following formula (1) and having characteristic peaks at Bragg angles (2θ±0.2°) of 7.2° and 25.9° in X-ray diffraction with the characteristic Cu Kα line, or a tautomer thereof:

(1):

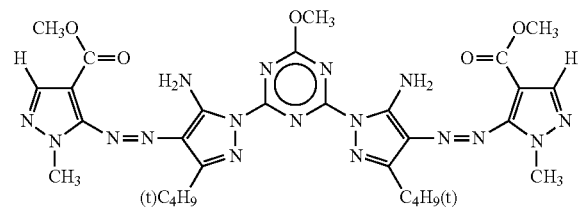

(2). The azo pigment composition according to (1), which further comprises an azo pigment represented by the formula (1) and in a crystal form having characteristic peaks at Bragg angles (2θ±0.2°) of 6.6°, 8.9°, 11.7°, 18.4°, 25.7°, and 26.7° in X-ray diffraction with the characteristic Cu Kα line, or a tautomer thereof in a content of from 0 to 50% by weight.

(3). The azo pigment composition according to (2), wherein the content of the azo pigment represented by the formula (1) and in the crystal form having characteristic peaks at Bragg angles (2θ±0.2°) of 6.6°, 8.9°, 11.7°, 18.4°, 25.7°, and 26.7° in X-ray diffraction with the characteristic Cu Kα line, or the tautomer thereof is from 0 to 20% by weight.

(4). The azo pigment composition according to (2) or (3), wherein the content of the azo pigment represented by the formula (1) and in the crystal form having characteristic peaks at Bragg angles (2θ±0.2°) of 6.6°, 8.9°, 11.7°, 18.4°, 25.7°, and 26.7° in X-ray diffraction with the characteristic Cu Kα line, or the tautomer thereof is from 0 to 10% by weight.

(5). A process for producing an azo pigment composition comprising at least one azo pigment represented by the formula (1) and having characteristic peaks at Bragg angles (2θ±0.2°) of 7.2° and 25.9° in X-ray diffraction with the characteristic Cu Kα line, or a tautomer thereof, the process comprising a step of conducting a diazo coupling reaction between a diazonium salt derived from a heterocyclic amine represented by the formula (2) and a compound represented by the formula (3):

(2):

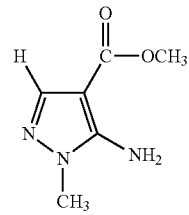

(3):

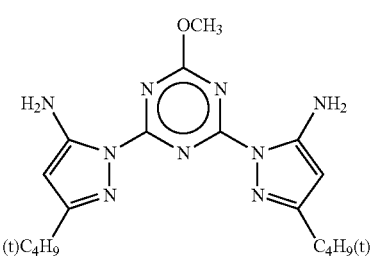

(1):

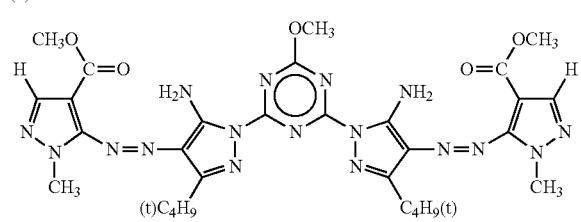

(6). The production process according to (5), which further comprises a step of conducting after-treatment:

(7). An azo pigment composition comprising at least one azo pigment represented by the formula (1) and having characteristic peaks at Bragg angles (2θ±0.2°) of 7.2° and 25.9° in X-ray diffraction with the characteristic Cu Kα line, or a tautomer thereof, the azo pigment or tautomer thereof being produced by a production process of (5) or (6).

(1):

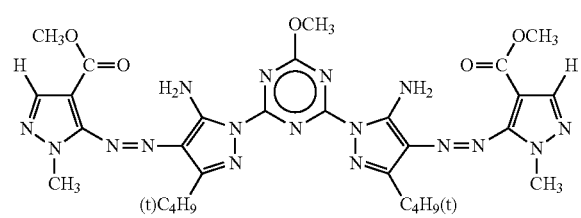

(8). A pigment dispersion comprising the azo pigment composition described in any one of (1) to (4), and (7).

(9). The pigment dispersion according to (8), wherein the azo pigment contained in the azo pigment composition has a volume-average particle size of from 0.01 μm to 0.2 μm.

(10). A coloring composition comprising as a colorant the azo pigment composition described in any one of (1) to (4), and (7).

(11). An ink for inkjet recording, comprising as a colorant an azo pigment composition described in any one of (1) to (4), and (7).

According to the present invention, there is provided an azo pigment having excellent coloring characteristics such as tinctorial strength and hue and having excellent dispersibility and dispersion stability. A pigment dispersion having excellent coloring characteristics, dispersibility, and dispersion stability can be obtained by dispersing the pigment of the invention in various media. The pigment dispersion can be used as a coloring material having excellent light fastness for, for example, an ink for printing such as inkjet printing, a color toner for electrophotograph, a display such as LCD or PDP, a color filter to be used in, photographing equipment such as CCD, a paint, and a colored plastic.

BEST MODE FOR CARRYING OUT THE INVENTION

Figure 1:
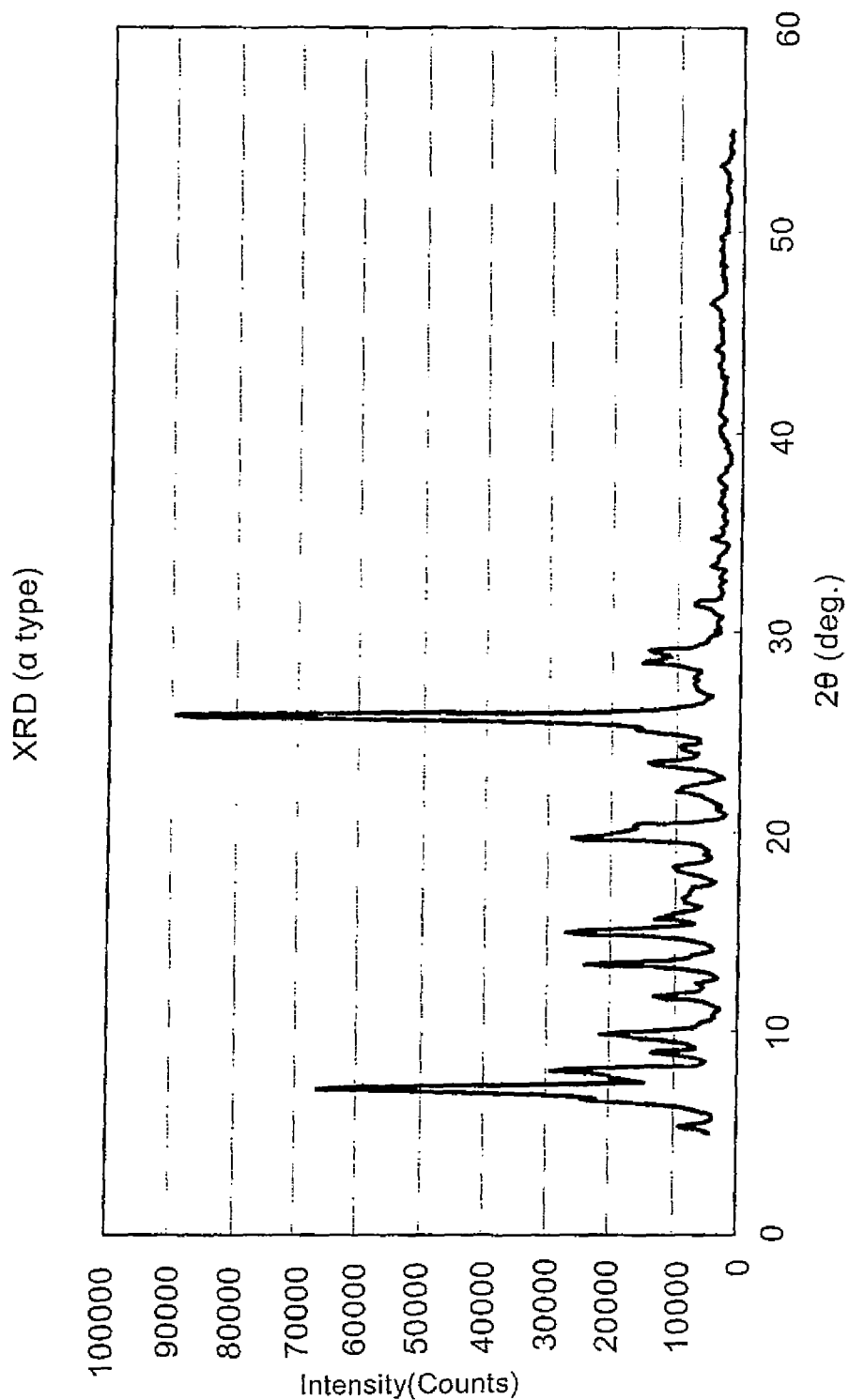
FIG. 1 is an X-ray diffraction pattern of an azo pigment (1) synthesized according to Synthesis Example 1.

The present invention will be described in detail below. The azo pigment composition of the invention contains at least one azo pigment represented by the following formula (1) and in a crystal form having characteristic peaks at Bragg angles (2θ±0.2°) of 7.2° and 25.9° in X-ray diffraction with the characteristic Cu Kα line, or a tautomer thereof.

In this specification, the azo pigment represented by the following formula (1) and having characteristic peaks at Bragg angles (2θ±0.2°) of 7.2° and 25.9° in X-ray diffraction with the characteristic Cu Kα line will be hereinafter referred to as an α-type crystal form azo pigment.

Also, in this specification, an azo pigment represented by the following formula (1) and having characteristic peaks at Bragg angles (2θ±0.2°) of 6.6°, 8.9°, 11.7°, 18.4°, 25.7°, and 26.7° in X-ray diffraction with the characteristic Cu Kα line will be hereinafter referred to as a β-type crystal form azo pigment.

(1):

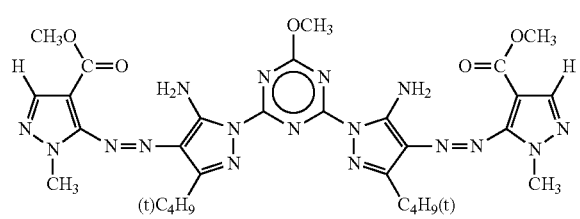

In the invention, with an azo pigment composition of the α-type crystal form azo pigment represented by the above formula (1) and the β-type crystal form azo pigment contained in the α-type crystal form azo pigment, the contents of the α-type crystal form azo pigment and the β-type crystal form azo pigment can easily be determined by, for example, measuring the X-ray diffraction pattern of a sample composition, and comparing the intensity of the peak at a Bragg angle (2θ±0.2°) of 7.2° and the intensity of the peak at a Bragg angle (2θ±0.2°) of 6.6° with those obtained by measuring X-ray diffraction of standard samples prepared by mixing a standard α-type crystal form azo pigment with a standard β-type crystal form azo pigment in arbitrary weight ratios. In the invention, the measurement of X-ray diffraction is conducted according to Japanese Industrial Standards JISK0131 (General Rule of X-ray diffractiometry) using a powder X-ray diffractometer, RINT 2500 (manufactured by Rigaku Industrial Corp.).

In the invention, as a process for obtaining an azo pigment composition containing the β-type crystal form azo pigment, there is illustrated a process of conducting a step of azo coupling reaction between a diazonium salt derived from a heterocyclic amine represented by the foregoing formula (2) and a compound represented by the foregoing formula (3) while controlling the reaction conditions (solvent species, pH value, reaction temperature, reaction time, etc.). Further, the composition can be obtained with ease by subjecting the azo pigment obtained in the above-described step to an after-treatment while controlling the after-treating conditions (solvent species, pH value, reaction temperature, reaction time, etc.).

The azo pigment composition of the invention may alternatively be produced by separately producing the α-type crystal form azo pigment and the (s-type crystal form azo pigment and mixing them with any favorable ratio. Further, as other process for producing the azo pigment of the invention, an azo pigment composition with a favorable mixing composition ratio may be directly produced by controlling the reaction conditions during the production of the azo pigment composition.

In the case where the azo pigment is in a single crystal form, distance between molecules is so close that intermolecular action becomes strong. As a result, the pigment shows an increased solvent resistance, an increased heat resistance, an increased resistance to gases, and an increased print density and, further, an expanded color reproducible region. The α-type crystal form azo pigment is of a crystal form having characteristic X-ray diffraction peaks at Bragg angles (2θ±0.2°) of 7.2° and 25.9°. A crystal form having characteristic X-ray diffraction peaks at Bragg angles (2θ±0.2°) of 7.2°, 15.0°, 19.8°, and 25.9° is preferred. In particular, a crystal form having characteristic X-ray diffraction peaks at Bragg angles (2θ±0.2°) of 7.2°, 8.2°, 10.0°, 13.4°, 15.0°, 19.8°, and 25.9° is more preferred.

In view of sharpness of particle size distribution of the pigment dispersion, the peak height at a Bragg angle (2θ±0.2°) of 6.6° in X-ray diffraction with the characteristic Cu Kα line is preferably more than 0.00001 when the peak height at 7.6° is taken as 1. Also, the peak height at 6.4° is preferably less than 0.2 in view of color reproducibility with respect to hue, since it serves to suppress excessively reddish tone. Therefore, the peak height at a Bragg angle (2θ±0.2°) of 6.6° in X-ray diffraction with characteristic Cu Kα line is preferably not less than 0.00001 and not more than 0.2, more preferably not less than 0.0001 and not more than 0.1, most preferably not less than 0.0001 and not more than 0.05, when the peak height at 7.6° is taken as 1.

The azo pigment composition preferably further contains an azo pigment represented by the following formula (1) and having characteristic peaks at Bragg angles (2θ±0.2° of 6.6°, 8.9°, 11.7°, 18.4°, 25.7°, and 26.7 in X-ray diffraction with the characteristic Cu Kα line (β-type crystal form azo pigment) or a tantomer thereof in a content of from 0 to 50% by weight, more preferably from 0 to 20% by weight, still more preferably from 0 to 10% by weight. Also, the content is preferably 0.01% by weight or more, more preferably 0.1% by weight or more.

An azo pigment composition containing the β-type crystal form azo pigment in a content of the above-described range is preferred since, when the azo pigment composition is used in, for example, a dispersion, a coloring composition or in an ink for inkjet recording, excellent control of particle size distribution of the pigment dispersion (for example, control of liquid properties of a pigment ink) can be attained.

Also, the length of the long axis of primary particles of the α-type crystal form azo pigment represented by the foregoing formula (1) observed under a transmission microscope is preferably from 0.01 μm to 30 μm, more preferably from 0.02 μm to 15 μm, particularly preferably from 0.03 μm to 1 μm.

In the case where the length of the long axis of the primary particles observed under a transmission microscope is not less than 0.01 good fastness to light or ozone and, when formed into a pigment dispersion, good dispersibility can be realized with more certainty. On the other hand, in the case where the length is not more than 30 μm, there scarcely results an overdispersion state (state where primary particles are destroyed) upon dispersing the particles to attain desired volume-average particle size, thus active surfaces being scarcely laid bare on the pigment particle surface. Hence, aggregation of pigment particles scarcely occurs, which serves to realize good storage stability of the pigment dispersion with more certainty.

When the size of the primary particles is controlled within the above-described range, there result strong intramolecular and intermolecular mutual action, thus pigment particles forming strong, firm, and stable three-dimensional network being obtained. Such pigment particles show high fastness to light, heat, moisture, and an oxidizing gas, and colored materials using the pigment dispersion have excellent storage stability, thus such pigment particles being preferred.

The volume-average particle size of the pigment dispersion containing the pigment composition of the invention can be measured by using a Nanotruck UPA Particle Size Analyzer (UPA-EX 150; manufactured by Nikkiso Co., Ltd.). The measurement can be conducted by, for example, placing 3 ml of a pigment dispersion in a measurement cell and performing operation according to a given measuring manner. Additionally, as parameters to be inputted upon measurement, an ink viscosity is used as the viscosity, and a density of the pigment is used as the density of dispersed particles.

The average particle size of the α-type crystal form azo pigment is preferably from 0.01 μm to 30 μm, more preferably from 0.02 μm to 10 μm, most preferably from 0.03 μm to 1 μm.

When the particle size is within the above-described range, there result prints with high density, an increased stability of a dispersion thereof, an improved color reproducibility in a mixed area of red or green, and a high transparency and, upon printing through inkjet printing or the like, clogging of a nozzle scarcely occurs, thus such particle size being preferred. In addition, conversely, aggregation scarcely occurs, and stability with time of the dispersion is high, thus such particle size being preferred.

Adjustment of the volume-average, particle size of the pigment dispersion containing the pigment composition of the invention to the above-described range can be conducted with ease by appropriately combining the pigment-dispersing conditions to be described hereinafter.

A process for producing an azo pigment composition containing at least one of an azo pigment represented by the following formula (1) and in a crystal form having characteristic peaks at Bragg angles (2θ±0.2°) of 7.2° and 25.9° in X-ray diffraction with the characteristic Cu Kα line, or a tautomer thereof will be described in detail below.

The process for producing the azo pigment composition is characterized by involving a step of azo coupling reaction between a diazonium salt derived from a heterocyclic amine represented by the following formula (2) and a compound represented by the following formula (3).

(2):

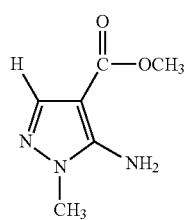

(3):

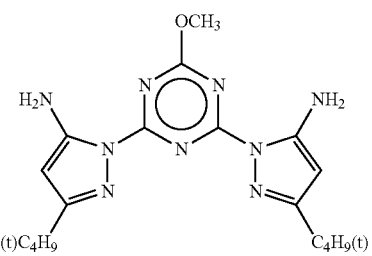

(1):

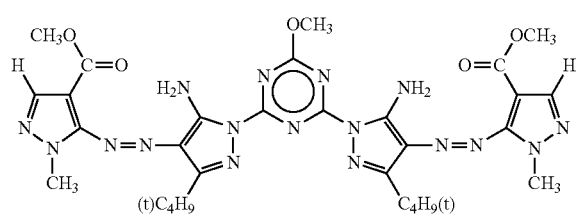

Preparation of the Diazonium Salt and Coupling Reaction Between the diazonium salt and the compound represented by formula (3) can be conducted in a conventional manner.

For preparation of the diazonium salt of the heterocyclic amine represented by formula (2), there may be applied, for example, a conventional process for preparing a diazonium salt using a nitrosonium ion source such as nitrous acid, nitrite or nitrosylsulfuric acid in a reaction medium containing an acid (for example, hydrochloric acid, sulfuric acid, phosphoric acid acetic acid, propionic acid, methanesulfonic acid, or trifluoromethanesulfonic acid).

As examples of more preferred acids, there are illustrated acetic acid, propionic acid, methanesulfonic acid, phosphoric acid, and sulfuric acid, which may be used alone or in combination thereof. Of these, phosphoric acid, a combination of acetic acid and sulfuric acid, a combination of acetic acid and propionic acid, and a combination of acetic acid, propionic acid and sulfuric acid are more preferred, with a combination of acetic acid and propionic acid and a combination of acetic acid, propionic acid, and sulfuric acid being particularly preferred.

As preferred examples of the reaction medium (solvent), organic acids and inorganic acids are preferred for use and, in particular, phosphoric acid, sulfuric acid, acetic acid, propionic acid, and methanesulfonic acid are preferred, with acetic acid and/or propionic acid being particularly preferred.

As a preferred example of the nitrosonium ion source, use of nitrosylsulfuric acid in a reaction medium containing the above-described preferred acid enables preparation of a diazonium salt with stability and efficiency.

The amount of the solvent to be used is preferably from 0.5- to 50-fold amount by weight, more preferably from 1- to 20-fold amount by weight, particularly preferably from 3- to 15-fold amount by weight, based on the amount of a diazo component of formula (2).

In the invention, the diazo component of formula (2) may be in a state of being dispersed in the solvent or, with some kinds of the diazo components, in a state of a solution.

The amount of the nitrosonium ion source to be used is preferably from 0.95 to 5.0 equivalent weight, more preferably from 1.00 to 3.00 equivalent weight, particularly preferably from 1.00 to 1.10 equivalent weight, in terms of the diazo component.

The reaction temperature is preferably from −15° C. to 40° C., more preferably from −5° C. to 35° C., still more preferably from −0° C. to 30° C. In case when the reaction temperature is lower than −10° C., the reaction rate becomes so small that the time required for the synthesis becomes seriously prolonged, thus such temperature not being preferred in view of production cost whereas, in case when the synthesis is conducted at a temperature higher than 40° C., the amount of produced by-products is increased, thus such temperature not being preferred.

The reaction time is preferably from 30 minutes to 300 minutes, more preferably from 30 minutes to 200 minutes, still more preferably from 30 minutes to 150 minutes.

[Coupling Reaction Step]

The coupling reaction step can be conducted in an acidic reaction medium to a basic reaction medium. Preferably, however, for the azo pigment of the invention, the coupling reaction step is conducted in an acidic to neutral reaction medium. In particular, when conducted in an acidic reaction medium, the coupling reaction gives an azo pigment with good efficiency without decomposition of the diazonium salt.

As preferred examples of the reaction medium (solvent), organic acids, inorganic acids, and organic solvents may be used, with organic solvents being particularly preferred. As such solvents, those solvents are preferred upon reaction, do not cause liquid separation phenomenon but form a uniform solution. Examples thereof include alcoholic organic solvents such as methanol, ethanol, propanol, isopropanol, butanol, t-butyl alcohol, and amyl alcohol; ketone series organic solvents such as acetone and methyl ethyl ketone; diol series organic solvents such as ethylene glycol, diethylene glycol, triethylene glycol, propylene glycol, dipropylene glycol, and 1,3-propanediol; ether series organic solvents such as ethylene glycol monomethyl ether, ethylene glycol monoethyl ether, and ethylene glycol diethyl ether; tetrahydrofuran; dioxane; and acetonitrile. These solvents may be a mixture of two or more thereof.

Organic solvents having a polarity parameter (ET) of 40 or more are preferred. Of them, glycol series solvents having two or more hydroxyl groups in the molecule thereof, alcoholic solvents containing 3 or less carbon atoms, and ketone series solvents containing a total of 5 or less carbon atoms are more preferred, with alcoholic solvents containing 2 or less carbon atoms (for example, methanol and ethylene glycol) and ketone series solvents containing a total of 4 or less carbon atoms (for example, acetone and methyl ethyl ketone) being still more preferred. Mixed solvents thereof are also included.

The amount of the solvent to be used is preferably from 1- to 100-fold amount by weight, more preferably from 1- to 50-fold amount by weight, still more preferably from 2- to 30-fold amount by weight, based on the coupling component represented by the foregoing formula (3).

In the invention, the coupling component of formula (3) may be in a state of being dispersed in the solvent or, with some kinds of the coupling components, in a state of a solution.

The amount of the coupling component to be used is preferably from 0.95 to 5.0 equivalent weight, more preferably from 1.00 to 3.00 equivalent weight, particularly preferably from 1.00 to 1.50 equivalent weight, in terms of the diazo coupling moiety.

The reaction temperature is preferably from −30° C. to 30° C., more preferably from −15° C. to 10° C., still more preferably from −10° C. to 5° C. In case when the reaction temperature is lower than −30° C., the reaction rate becomes so small that the time required for the synthesis becomes seriously prolonged, thus such temperature not being preferred in view of production cost whereas, in case when the synthesis is conducted at a temperature higher than 30° C., the amount of produced by-products is increased, thus such temperature not being preferred.

The reaction time is preferably from 30 minutes to 300 minutes, more preferably from 30 minutes to 200 minutes, still more preferably from 30 minutes to 150 minutes.

In the process of the invention for producing the azo pigment composition, the product obtained by these reactions (crude azo pigment) may be used after being treated according to an after-treatment for common organic synthesis reactions and optionally after being purified.

That is, a product isolated from the reaction system may be used without purification or after being subjected to purifying through a single operation of, or a combination of, recrystallization, salt formation, etc.

Also, after completion of the reaction, there may be conducted a single of, or a combination of, the procedures that the reaction solvent may or may not be distilled off, that the reaction product may be poured into water or ice-water, that the resulting solution may or may not be neutralized, and that the liberated portion or the extract obtained by extracting with an organic solvent/water solution may or may not be purified through recrystallization, crystallization, salt formation or the like.

The process for producing the azo pigment composition of the invention will be described in more detail below.

A process for producing the azo pigment composition of the invention is characterized by conducting a coupling reaction between a diazonium compound prepared by diazotizing a heterocyclic amine represented by the foregoing formula (2) and a compound represented by the foregoing formula (3) after dissolving the compound of formula (3) in an organic solvent.

The diazotization reaction of the heterocyclic amine represented by the foregoing formula (2) may be conducted by, for example, reacting the amine with a reagent such as sodium nitrite or nitrosylsulfuric acid in an acidic solvent such as sulfuric acid, phosphoric acid, or acetic acid at a temperature of 15° C. or lower than that for a period of from about 10 minutes to about 6 hours. The coupling reaction is conducted preferably by reacting the diazonium salt obtained by the above-described process with the compound represented by the foregoing formula (3) at 40° C. or lower than that, preferably 15° C. or lower than that, for a period of from about 10 minutes to about 12 hours.

The aforesaid control of tautomerization and/or polymorphism can be attained through production conditions upon coupling reaction. As a process for producing a pigment composition which contains as a major component α-form crystals of the invention which composition is a more preferred embodiment of the invention, it is preferred to employ, for example, a process of the invention wherein the coupling reaction is conducted after once dissolving the compound represented by the foregoing formula (3) in an organic solvent. As the organic solvent which can be used here, there are illustrated, for example, alcoholic solvents and ketone series solvents. As the alcoholic solvents, methanol, ethanol, isopropanol, ethylene glycol, and diethylene glycol are preferred. Of these, methanol is particularly preferred. As the ketone series solvents, acetone, methyl ethyl ketone, and cyclohexanone are preferred. Of these, acetone is particularly preferred.

Another process for producing the azo pigment composition of the invention is characterized by conducting the coupling reaction between a diazonium compound prepared by diazotizing a heterocyclic amine represented by the foregoing formula (2) and a compound represented by the foregoing formula (3) in the presence of a polar aprotic solvent.

A pigment, composition containing as a major component α-form crystals of the invention can also be produced with good efficiency by conducting the coupling reaction in the presence of a polar aprotic solvent. Examples of the polar aprotic solvent include N,N-dimethylformamide, N,N-dimethylacetamide, N-methyl-2-pyrrolidone, dimethylsulfoxide, tetramethylurea, acetone, methyl ethyl, ketone, acetonitrile, and a mixed solvent thereof. Of these solvents, acetone, methyl ethyl ketone, N,N-dimethylacetamide, and acetonitrile are particularly preferred. In the case of using these solvents, the compound of the foregoing formula (3) may or may not be completely soluble in the solvent.

The compound obtained by the above-described production process may or may not be subjected to adjustment of pH by adding a base as a purifying step according to use. In the case of adjusting pH, the pH is preferably from 4 to 10. Of them, a pH of from 5 to 8 is more preferred, with a pH of 5.5 to 7.5 being particularly preferred.

When the pH is 10 or less than that, the resulting hue does not give an increased reddish tone, thus such pH being preferred in view of hue. When the pH is 4 or more, there scarcely occurs a problem of, for example, corrosion of a nozzle in the case of being used as an ink for inkjet recording, thus such pH being preferred.

The above-described production process gives the compound represented by the foregoing formula (1) as a crude azo pigment (crude).

The invention also relates to an azo pigment composition produced by the above-described production process.

[After-Treating Step]

The production process of the invention preferably includes a step of after-treatment (finishing). As the method of the after-treating step, there are illustrated, for example, pigment particle size-controlling step by milling treatment such as solvent-salt milling, salt milling, dry milling, solvent milling or acid pasting, or by treatment of heating in a solvent; and surface-treating step with a resin, a surfactant, a dispersing agent, etc.

The term "finishing" as used in the invention means a treatment for making uniform the crystal form, size and shape of particles, and the like.

The compound of the invention represented by formula (1) is preferably subjected to the solvent heating treatment and/or the solvent-salt milling as the after-treatment. For example, α-type crystal form azo pigment can be produced by refluxing in a water-free organic solvent.

As a solvent to be used in the solvent heating treatment, there are illustrated, for example, water; aromatic hydrocarbon series solvents such as toluene and xylene; halogenated hydrocarbon series solvents such as chlorobenzene and o-dichlorobenzene; alcoholic solvents such as isopropanol and isobutanol; polar aprotic organic solvents such as N,N-dimethylformamide, N,N-dimethylacetamide, N-methyl-2-pyrrolidone, acetone, methyl ethyl ketone, and acetonitrile; glacial Acetic acid; pyridine; and a mixture thereof. An inorganic or organic acid or base may further be added to the above-described solvents. The temperature of the solvent heating treatment varies depending upon the desired primary particle size of the pigment, but is preferably from 40 to 150° C., more preferably from 60 to 100° C. The treating time is preferably from 30 minutes to 24 hours.

As the solvent-salt milling, there is illustrated, for example, the procedure wherein a crude azo pigment, an inorganic salt, and an organic solvent which does not dissolve them are placed in a kneader, and knead-milling of the mixture is conducted therein. As the inorganic salt, water-soluble inorganic salts can preferably be used. For example, inorganic salts such as sodium chloride, potassium chloride, and sodium sulfate are preferably used. Also, it is more preferred to use inorganic salts having an average particle size of from 0.5 to 50 µm. The amount of the inorganic salt to be used is preferably a 3- to 20-fold amount by weight, more preferably a 5- to 15-fold amount by weight, based on the crude pigment. As the organic solvent, water-soluble organic solvents can preferably be used and, since the solvent becomes easily vaporizable due to an increase in temperature upon kneading, high-boiling solvents are preferred in view of safety. Examples of such organic solvents include diethylene glycol, glycerin, ethylene glycol, propylene glycol, liquid polyethylene glycol, liquid polypropylene glycol, 2-(methoxymethoxy)ethanol, 2-butoxyethanol, 2-(isopentyloxy)ethanol, 2-(hexyloxy)ethanol, diethylene glycol monomethyl ether, diethylene glycol monoethyl ether; diethylene glycol monobutyl ether, triethylene glycol, triethylene glycol monomethyl ether, 1-methoxy-2-propanol, 1-ethoxy-2-propanol, dipropylene glycol, dipropylene glycol monomethyl ether, dipropylene glycol monomethyl ether, dipropylene glycol, and a mixture thereof. The amount of the water-soluble organic solvent to be used is preferably a 0.1- to 5-fold amount based on the crude azo pigment. The kneading temperature is preferably from 20 to 130° C., particularly preferably from 40 to 110° C. As a kneader, there can be used, for example, a kneader or a mix muller.

[Pigment Dispersion]

The pigment dispersion of the invention is characterized in that it contains at least one of the azo pigments. Thus, there can be obtained a pigment dispersion having excellent coloring characteristics, durability, and dispersion stability.

The pigment dispersion of the invention may be aqueous or non-aqueous, but is preferably an aqueous pigment dispersion. As the aqueous liquid for dispersing the pigment in the aqueous pigment dispersion of the invention, a mixture containing water as a major component and, as needed, a hydrophilic organic solvent can be used. Examples of the hydrophilic organic solvent include alcohols such as methanol, ethanol, propanol, isopropanol, butanol, isobutanol, sec-butanol, t-butanol, pentanol, hexanol, cyclohexanol, and benzyl alcohol; polyhydric alcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol, and thiodiglycol; glycol derivatives such as ethylene glycol monomethyl ether, ethylene glycol monoehyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monoethyl ether, and ethylene glycol monophenyl ether; amines such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, and tetramethylpropylenediamine; formamide; N,N-dimethylformamide; N,N-dimethylacetamide; dimethylsulfoxide; sulfolane; 2-pyrrolidone; N-methyl-2-pyrrolidone; N-vinyl-2-pyrolidone; 2-oxazolidone; 1,3-dimethyl-2-imidazolidinone; acetonitrile; and acetone.

Further, the aqueous pigment dispersion of the invention may contain an aqueous resin. As the aqueous resin, there are illustrated water-soluble resins which dissolve in water, water-dispersible resins which can be dispersed in water, colloidal dispersion resins, and a mixture thereof. Specific examples of the aqueous resins include acryl series resins, styrene-acryl series resins, polyester resins, polyamide resins, polyurethane resins, and fluorine-containing resins.

Further, in order to improve dispersibility of the pigment and quality of image, a surfactant and a dispersing agent may be used. As the surfactant, there are illustrated anionic, nonionic, cationic, and amphoteric surfactants, and any of them may be used. However, anionic or nonionic surfactants are preferred to use. Examples of the anionic surfactants include aliphatic acid salts, alkyl sulfate salts, alkylbenzene sulfonate salts, alkylnaphthalene sulfonate salts, dialkyl sulfosuccinate salts, alkyldiaryl ether disulfonate salts, alkyl phosphate salts, polyoxyethylene alkyl ether sulfate salts, polyoxyethylene alkylaryl ether sulfate salts, naphthalenesulfonic acid-formalin condensates, polyoxyethylene alkyl ether phosphate salts, glycerol borate fatty acid esters, and polyoxyethylene glycerol fatty acid esters.

Examples of the nonionic surfactants include polyoxyethylene alkyl ethers, polyoxyethylene alkylaryl ethers, polyoxyethylene-oxypropylene block copolymers, sorbitan fatty acid esters, polyoxyethylene sorbitan fatty acid esters, polyoxyethylene sorbitol fatty acid esters, glycerin fatty acid esters, polyoxyethylene fatty acid esters, polyoxyethylene alkylamines, fluorine-containing surfactants, and silicon-containing surfactants.

The non-aqueous pigment dispersion of the invention comprises the pigment represented by the foregoing formula (1) dispersed in a non-aqueous vehicle. Examples of resin to be used as the non-aqueous vehicle include petroleum resin, casein, shellac, rosin-modified maleic acid resin, rosin-modified phenol resin, nitrocellulose, cellulose acetate butyrate, cyclized rubber, chlorinated rubber, oxidized rubber, rubber hydrochloride, phenol resin, alkyd resin, polyester resin, unsaturated polyester resin, amino resin, epoxy resin, vinyl resin, vinyl chloride, vinyl chloride-vinyl acetate copolymer, acryl resin, methacryl resin, polyurethane resin, silicone resin, fluorine-containing resin, drying oil, synthetic drying oil, styrene/maleic acid resin, styrene/acryl resin, polyamide resin, polyimide resin, benzoguanamine resin, melamine resin, urea resin, chlorinated polypropylene, butyral resin, and vinylidene chloride resin. It is also possible to use a photo-curable resin as the non-aqueous vehicle.

Examples of the solvents to be used in the non-aqueous vehicles include aromatic solvents such as toluene, xylene, and methoxybenzene; acetate series solvents such as ethyl acetate, butyl acetate, propylene glycol monomethyl ether acetate, and propylene glycol monoethyl ether acetate; propionate series solvents such as ethoxyethyl propionate; alcoholic solvents such as methanol and ethanol; ether series solvents such as butyl cellosolve, propylene glycol monomethyl ether, diethylene glycol ethyl ether, and diethylene glycol dimethyl ether; ketone series solvents such as methyl ethyl ketone, methyl isobutyl ketone, and cyclohexanone; aliphatic hydrocarbon series solvents such as hexane; nitrogen-containing compound series solvents such as N,N-dimethylformamide, γ-butyrolactam, N-methyl-2-pyrrolidone, aniline, and pyridine; lactone series solvents such as γ-butyrolactone; and carbamic acid esters such as a 48:52 mixture of methyl carbamate and ethyl carbamate.

The pigment dispersion of the invention is obtained by dispersing the azo pigment and the aqueous or non-aqueous medium using a dispersing apparatus. As the dispersing apparatus, there can be used a simple stirrer, an impeller-stirring system, an in-line stirring system, a mill system (for example, colloid mill, ball mill, sand mill, beads mill, attritor, roll mill, jet mill, paint shaker, or agitator mill), a ultrasonic wave system, a high-pressure emulsion dispersion system (high-pressure homogenizer; specific commercially available apparatuses being Gaulin homogenizer, a microfluidizer, and DeBEE2000).

In the invention, the volume-average particle size of the pigment is preferably from 0.01 μm to 0.2 μm. Additionally, the term "volume-average particle size of the pigment" means the particle size of the pigment itself or, in the case where an additive such as a dispersing agent is adhered to the pigment particles, means the size of the particle with the additive being adhered thereto. In the invention, as an apparatus for measuring the volume-average particle size of the pigment, a particle size analyzer of Nanotrac UPA (UPA-EX150; manufactured by Nikkiso Co., Ltd.) is used. The measurement is conducted according to a predetermined measuring method by placing 3 ml of a pigment dispersion in a measuring cell. Additionally, with respect to parameters to be inputted upon measurement, an ink viscosity is used as a viscosity, and a pigment density is used as a density of the pigment.

The volume-average particle size of the pigment is more preferably from 20 nm to 200 nm, still more preferably from 30 nm to 180 nm, most preferably from 30 nm to 150 nm. When the volume-average particle size of the particles in the pigment dispersion is 20 nm or more, storage stability can be ensured whereas, when the volume-average particle size of the particles in the pigment dispersion is 200 nm or less, a sufficient optical density can be obtained.

The content of the pigment contained in the pigment dispersion of the invention is preferably in the range of from 1 to 35% by weight, more preferably in the range of from 2 to 25% by weight, most preferably in the range of from 5 to 15% by weight. When the content is 1% by weight or more, a sufficient image density can be obtained by using the pigment dispersion independently as an ink. When the content is 35% by weight or less, a sufficient dispersion stability can be obtained.

As uses of the azo pigments of the invention, there are illustrated image recording materials for forming images, particularly color images. Specifically, there are illustrated inkjet system recording materials to be described in detail below, heat-sensitive recording materials, pressure-sensitive recording materials, recording materials for the electro-photographic system, transfer system silver halide light-sensitive materials, printing inks, and recording pens, preferably inkjet system recording materials, heat-sensitive recording materials, and recording materials for the electro-photographic system, more preferably inkjet system recording materials.

In addition, the pigments can find application to color filters for recording and reproducing color images to be used in solid state imaging devices such as CCDs and in displays such as LCD and PDP and to a pigmenting solution for pigmenting various fibers.

The azo pigment of the invention may be used in an emulsion dispersion state or in a solid dispersion state according to the system wherein it is used.

[Coloring Composition]

The coloring composition of the invention contains the azo pigment composition of the invention as a colorant. The coloring composition of the invention can contain a medium and, in the case where a solvent is used as the medium, the composition is particularly appropriate as an ink for inkjet recording. The coloring composition of the invention can be prepared by using an oleophilic medium or an aqueous medium as the medium and dispersing the azo pigment of the invention in the medium. Preferred is the case of using the aqueous medium. The coloring composition of the invention includes a composition for an ink excluding the medium. The coloring composition of the invention may contain, as needed, other additives within the range of not spoiling the advantages of the invention. Examples of the other additives include known additives (described in JP-A-2003-306623) such as a drying-preventing agent (a wetting agent), an antifading agent, an emulsion stabilizer, a penetration accelerator, an ultraviolet ray absorbent, an antiseptic, an antifungal agent, a pH-adjusting agent, a surface tension-adjusting agent, an anti-foaming agent, a viscosity-adjusting agent, a dispersing agent, a dispersion stabilizer, a rust inhibitor, and a chelating agent. In the case of water-soluble inks, these various additives are added directly to the ink solution. In the case of oil-soluble ink compositions, it is general to add to a dispersion after preparing the azo pigment dispersion, but they may be added to an oil phase or an aqueous phase upon preparation.

[Ink]

Next, the ink of the invention will be described below.

The ink of the invention contains the pigment dispersion of the invention and is preferably prepared by mixing with a water-soluble solvent or water. However, in the case where no particular problems are involved, the pigment dispersion of the invention may be used as such.

The ink of the invention for inkjet recording contains the pigment dispersion of the invention, and the ink of the invention can also be used as an ink for inkjet recording.

Also, the coloring composition containing the pigment of the invention can preferably be used as an ink for inkjet recording.

The ink of the invention uses the pigment dispersion described above. The ink is preferably prepared by mixing with a water-soluble solvent or water. However, in the case where no particular problems are involved, the pigment dispersion of the invention may be used as such.

The ink of the invention uses the pigment dispersion described above. The ink is preferably prepared by mixing with a water-soluble solvent or water. However, in the case where no particular problems are involved, the pigment dispersion of the invention may be used as such.

[Ink for Inkjet Recording]

Next, the ink of the invention for inkjet recording will be described below. The ink of the invention for inkjet recording contains an azo pigment composition as a coloring material. The ink for inkjet recording (hereinafter also referred to as "ink") contains the pigment dispersion described above and is preferably prepared by mixing with a water-soluble solvent or water. However, in the case where no particular problems are involved, the pigment dispersion of the invention described above may be used as such.

In consideration of hue, color density, saturation, and transparency of an image formed on a recording medium, the content of the pigment dispersion in the ink is in the range of preferably from 1 to 100% by weight, particularly preferably from 3 to 20% by weight, most preferably from 3 to 10% by weight.

The pigment of the invention is contained in an amount of preferably from 0.1 part by weight to 20 parts by weight, more preferably from 0.2 part by weight to 10 parts by weight, still more preferably from 1 to 10 parts by weight, in 100 parts by weight of the ink. The ink of the invention may further contain other pigment in combination with the pigment of the invention. In the case of using two or more kinds of pigments, the total amount of the pigments is preferably within the above-described range.

The ink of the invention can be used for forming a full-color image as well as a mono-color image. In order to form the full-color image, a magenta tone ink, a cyan tone ink, and a yellow tone ink can be used and, further, a black tone ink can be used for adjusting tone.

Further, in the ink of the invention may be used other pigments in addition to the azo pigment of the invention. As yellow pigments to be applied, there are illustrated, for example, C.I.P.Y.-74, C.I.P.Y.-128, C.I.P.Y.-155, and C.I.P.Y.-213. As magenta pigments to be applied, there are illustrated C.I.P.V.-19 and C.I.P.R.-122. As cyan pigments to be applied, there are illustrated C.I.P.B.-15:3 and C.I.P.B.-15:4. Apart from these pigments, any pigment may be used as each pigment. As a black color material, there can be illustrated a dispersion of carbon black as well as disazo, trisazo, and tetrazo pigments.

As the water-soluble solvents to be used in the ink, polyhydric alcohols, polyhydric alcohol derivatives, nitrogen-containing solvents, alcohols, and sulfur-containing solvents are used.

Specific examples of the polyhydric alcohols include ethylene glycol, diethylene glycol, propylene glycol, butylenes glycol, triethylene glycol, 1,5-pentanediol, 1,2,6-hexanetriol, and glycerin.

Examples of the polyhydric alcohol derivatives include ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monobutyl ether, dipropylene glycol monobutyl ether, and an ethylene oxide adduct of diglycerin.

Also, examples of the nitrogen-containing solvents include pyrrolidone, N-methyl-2-pyrrolidone, cyclohexylpyrrolidone, and triethanolamine, examples of the alcohols include ethanol, isopropyl alcohol, butyl alcohol, and benzyl alcohol, and examples of the sulfur-containing solvents include thiodiethanol, thiodiglycerol, sulfolane, and dimethylsulfoxide. Besides, propylene carbonate and ethylene carbonate may also be used.

The water-soluble solvents to be used in the invention may be used alone or as a mixture of two or more thereof. As to the content of the water-soluble solvent, the solvent is used in an amount of from 1% by weight to 60% by weight, preferably from 5% by weight to 40% by weight, based on the total weight of the ink. In case when the content of the water-soluble solvent in the entire ink is less than 1% by weight, there might result an insufficient optical density in some cases whereas, in case when the content exceeds 60% by weight, there might result unstable jet properties of the ink liquid in some cases due to the large viscosity of the liquid.

The preferred physical properties of the ink of the invention are as follows. The surface tension of the ink is preferably from 20 mN/m to 60 mN/m, more preferably from 20 mN/m to 45 mN/m, still more preferably from 25 mN/m to 35 mN/m. In case when the surface tension is less than 20 mN/m, the liquid might, in some cases, overflow onto the nozzle surface of the recording head, thus normal printing not being performed. On the other hand, in case when the surface tension exceeds 60 mN/m, the ink might, in some cases, slowly penetrate into the recording medium, thus the drying time becoming longer. Additionally, the surface tension is measured under the environment of 23° C. and 55% RH by using a Wilhelmy surface tension balance as is the same as described above.

The viscosity of the ink is preferably from 1.2 mPa·s to 8.0 mPa·s, more preferably from 1.5 mPa·s to 6.0 mPa·s, still more preferably from 1.8 mPa·s to 4.5 mPa·s. In case when the viscosity is more than 8.0 mPa·s, ink ejection properties might, in some cases, be deteriorated. On the other hand, in case when the viscosity is less than 1.2 mPa·s, the long-term ejection properties might be deteriorated in some cases.

Additionally, the above-described viscosity (including that to be described hereinafter) is measured by using a rotational viscometer Rheomat 115 (manufactured by Contraves Co.) at 23° C. and a shear rate of $1,400 \text{ s}^{-1}$.

In addition to the above-mentioned individual components, water is added to the ink within an amount of providing the preferred surface tension and viscosity described above. The addition amount of water is not particularly limited, but is in the range of preferably from 10% by weight to 99% by weight, more preferably from 30% by weight to 80% by weight, based on the total weight of the ink.

Further, for the purpose of controlling characteristic properties such as improvement of ejection properties, there can be used, as needed, polyethyleneimine, polyamines, polyvinylpyrolidone, polyethylene glycol, cellulose derivatives such as ethyl cellulose and carboxymethyl cellulose, polysaccharides and derivatives thereof, water-soluble polymers, polymer emulsions such as an acrylic polymer emulsion, a polyurethane series emulsion, and a hydrophilic latex, hydrophilic polymer gels, cyclodextrin, macrocyclic amines, dendrimers, crown ethers, urea and derivatives thereof, acetamide, silicone surfactants, and fluorine-continuing surfactants.

Also, in order to adjust electrical conductivity and pH, there can be used compounds of alkali metals such as potassium hydroxide, sodium hydroxide, and lithium hydroxide; nitrogen-containing compounds such as ammonium hydroxide, triethanolamine, di ethanolamine, ethanolamine, and 2-amino-2-methyl-1-propanol; compounds of alkaline earth metals such as calcium hydroxide; acids such as sulfuric acid, hydrochloric acid, and nitric acid; and salts between a strong acid and a weak alkali, such as ammonium sulfate.

Besides, pH buffers, antioxidants, antifungal agents, viscosity-adjusting agents, electrically conductive agents, and ultraviolet ray absorbents may also be added as needed.

[Inkjet Recording Method, Inkjet Recording Apparatus, and Ink Tank for Inkjet Recording]

Inkjet recording method is a method of forming an image on the surface of a recording medium by using an ink for inkjet recording, and ejecting the ink onto the surface of the recording medium from a recording head according to record signals.

Also, an inkjet recording apparatus is an apparatus wherein an ink for inkjet recording is used and a recording head capable of ejecting the ink (if necessary, a processing solution) onto the surface of a recording medium is provided, with the ink being ejected onto the surface of the recording medium from the recording head. Additionally, the inkjet recording apparatus can feed the ink to the recording head, and may be equipped with an ink tank for inkjet recording (hereinafter also referred to as "ink tank") which is removable from the main body of the inkjet recording apparatus. In this case, the ink is contained in the ink tank for inkjet recording.

As the inkjet recording apparatus, an ordinary inkjet recording apparatus equipped with a printing system capable of using an ink for inkjet recording can be utilized. In addition, there may be employed an inkjet recording apparatus having mounted thereon a heater or the like for controlling drying of the ink, or an inkjet recording apparatus equipped with a transfer mechanism which ejects (print) an ink and a processing solution onto an intermediate body, and then transfers the image on the intermediate body onto a recording medium such as paper.

Also, as the ink tank for inkjet recording, any of conventionally known ink tank can be utilized as long as it is removable from the inkjet recording apparatus equipped with a recording head and has a constitution that it can feed, in a state of being mounted on the inkjet recording apparatus, an ink to a recording head.

In view of the effect of reducing blurring and inter-color bleeding, it is preferred to employ a thermal inkjet recording system or a piezo inkjet recording system. With the thermal inkjet recording system, an ink is heated upon ejection to have a low viscosity, and the temperature of the ink decreases when the ink reaches onto a recording medium, leading to a sharp increase in viscosity. This serves to provide the effect of reducing blurring and inter-color bleeding. On the other hand, with the piezo inkjet recording system, a liquid with high viscosity can be ejected and, since the liquid with high viscosity can suppress its spread in the direction of paper surface on a recording medium, it serves to provide the effect of reducing blurring and inter-color bleeding.

In the inkjet recording method (apparatus), replenishment (feeding) of the ink to the head is conducted preferably from an ink tank filled with an ink liquid (including, as needed, a processing solution tank). This ink tank is preferably a cartridge system tank which is removable from the main body of the apparatus. Replenishment of the ink can be conducted with ease by exchanging the cartridge system ink tank.

[Color Toner]

The content of the azo pigment in 100 parts by weight of a color toner is not particularly limited, but is preferably 0.1 part by weight or more, more preferably from 1 to 20 parts by weight, most preferably from 2 to 10 parts by weight. As a binder resin for a color toner into which the azo pigment is to be introduced, any of all binders that are commonly used may be used. Examples thereof include styrene series resins, acryl series resins, styrene/acryl series resins, and polyester resins.

For the purpose of improving flowability or for controlling electrostatic charge, inorganic fine powders or organic fine particles may be externally added to the toner. Silica fine particles and titania fine particles surface-treated with a coupling agent containing an alkyl group are preferably used. Additionally, these have a number-average primary particle size of preferably from 10 to 500 nm, and are added to the toner in a content of preferably from 0.1 to 20% by weight.

As the release agent, any of conventionally used release agents can be used. Specific examples thereof include olefins such as low molecular polypropylene, low molecular polyethylene, and ethylene-propylene copolymer, and waxes such as microcrystalline wax, carnauba wax, sazol wax, and paraffin wax. The addition amount thereof is preferably from 1 to 5% by weight in the toner.

The charge controlling agent may be added as needed and, in view of color forming properties, colorless agents are preferred. Examples thereof include those of quaternary ammonium salt structure and those of calixarene structure.

As the carrier, any of non-coated carriers constituted by particles of magnetic material (such as iron or ferrite) alone and resin-coated carriers comprising magnetic material particles whose surface is coated with a resin may be used. The average particle size of the carrier is preferably from 30 to 150 µm in terms of volume-average particle size.

The image-forming method to which the toner of the invention is applied is not particularly limited, and examples thereof include an image-forming method by repeatedly forming a color image and transferring it, a method of forming a color image by successively transferring an image formed on an electro-photographic photoreceptor, and a method of forming a color image by successively transferring an image formed on an electro-photographic photoreceptor onto an intermediate transfer body to form a color image on the intermediate transfer body and transferring the color image onto an image-forming member such as paper.

(Thermally Recording (Transferring) Material)

The thermally recording material is constituted by an ink sheet comprising a support having coated thereon the pigment of the invention together with a binder, and an image-receiving sheet for immobilizing the pigment traveled in conformity with a thermal energy added from a thermal head according to image-recording signals. The ink sheet can be formed by dispersing the azo pigment of the invention in a solvent together with a binder as fine particles in a solvent to prepare an ink liquid, coating the ink on a support, and properly drying the coated ink. The amount of the ink to be coated on the support is not particularly limited, but is preferably from 30 to 1000 mg/m$^2$. As preferred binder resin, ink solvent, support and, further, an image-receiving sheet, those which are described in JP-A-7-137466 can preferably be used.

In using the thermally recording material as a thermally recording material capable of recording a full color image, it is preferred to form it by successively coating on a support a cyan ink sheet containing a thermally diffusible cyan colorant which can form a cyan image, a magenta ink sheet containing a thermally diffusible magenta colorant which can form a magenta image, and a yellow ink sheet containing a thermally diffusible yellow colorant which can form a yellow image. Also, an ink sheet containing a black image-forming substance may further be formed as needed.

[Color Filter]

As a method for forming a color filter, there are a method of first forming a pattern by a photo resist and then pigmenting, and a method of forming a pattern by a photo resist containing a colorant as described in JP-A-4-163552, JP-A-4-128703, and JP-A-4-175753. As a method to be employed in the case of introducing the colorant of the invention into a color filter, any of these methods may be employed. As a preferred method, there can be illustrated a method of forming a color filter which comprises exposing through a mask a positive-working composition comprising a thermosetting composition, a quinonediazide compound, a cross-linking agent, a colorant, and a solvent and being coated on a substrate; developing the exposed portion to form a positive resist pattern, exposing the whole positive resist pattern, then curing the exposed resist pattern, as described in JP-A-4-175753 and JP-A-6-35182. Also, an RGB primary color-based color filter or a YMC complementary color-based color filter can be obtained by forming a black matrix according to a conventional manner. With the color filter, too, there are no limits as to the amount of the pigment to be used, but a content of from 0.1 to 50% by weight is preferred.

As the thermosetting resin, the quinonediazide compound, the cross-linking agent, and the solvent to be used in forming the color filter, and the amounts thereof to be used, those which are described in the aforesaid patent documents can preferably be used.

The present invention is described in more detail with reference to the following examples, but the invention should not be construed as being limited thereto. Additionally, "parts" as used in Examples are by weight.

EXAMPLES

Measurement of the X-ray diffraction of the pigment composition of the invention containing the α-type crystal form pigment as a major component is conducted according to Japanese Industrial Standards JISK0131 (General Rule of X-ray diffractiometry) under the following conditions using a powder X-ray diffractometer, RINT 2500 (manufactured by Rigaku Industrial Corp.) and Cu Kα line.

Measuring apparatus used: automatic X-ray diffractometer, RENT 2500 (manufactured by Rigaku Industrial Corp.)
X-ray tube: Cu
Tube voltage: 55 KV Tube current:. 280 mA
Scanning method: 2θ/θ scan
Scanning speed: 6 deg./min
Sampling interval: 0.100 deg.
Starting angle (2θ): 5 deg.
Stopping angle (2θ): 55 deg.
Divergence slit: 2 deg.
Scattering slit: 2 deg.
Receiving slit: 0.6 mm
An upright goniometer is used.

Synthesis Example 1

Synthesis of an Azo Pigment Composition Containing α-Type Crystal Form as a Major Component

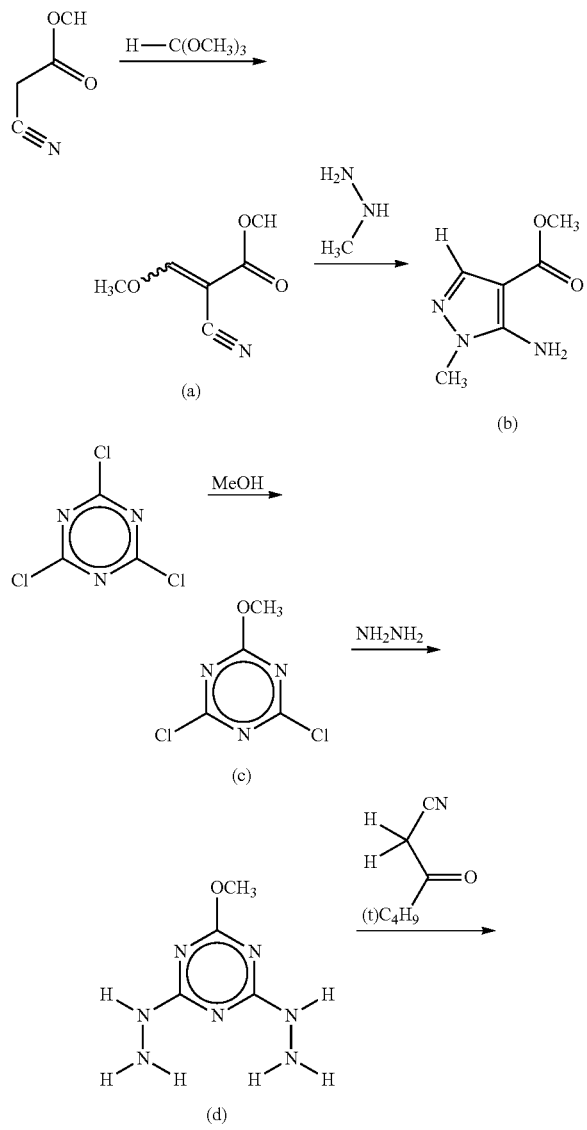

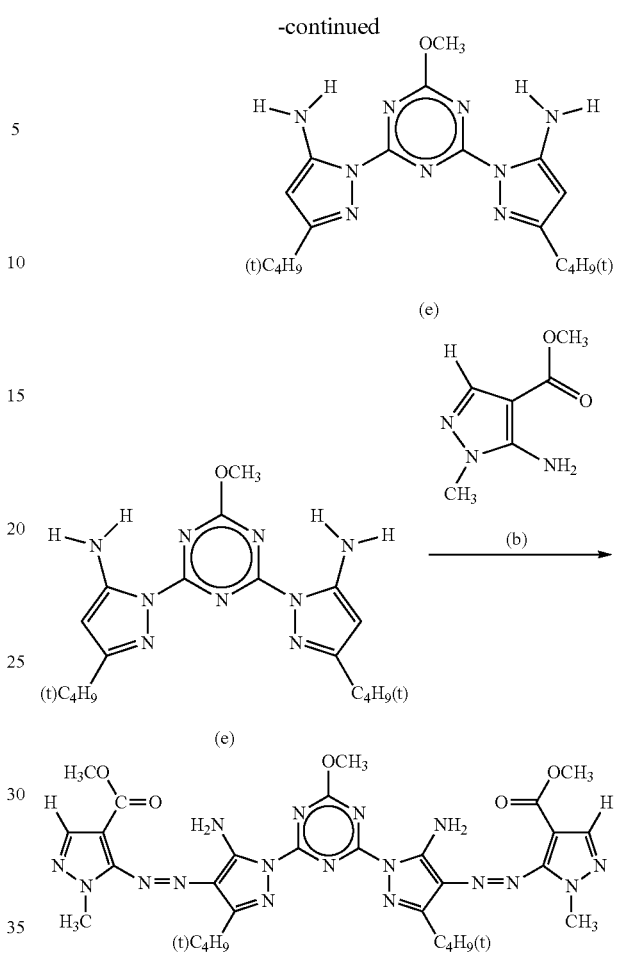

(1) Synthesis of Intermediate (a)

42.4 g (0.4 mol) of trimethyl orthoformate, 20.4 g (0.2 mol) of glacial acetic acid, and 0.5 g of p-toluenesulfonic acid are added to 29.7 g (0.3 mol) of methyl cyanoacetate, and the resulting mixture is heated to 110° C. (external temperature), followed by stirring for 20 hours with distilling off low-boiling components produced from the reaction system. The resulting reaction solution is concentrated under reduced pressure, and is subjected to purification by silica gel column chromatography to obtain 14.1 g (yellow powder; yield: 30%) of the intermediate (a). Results of NMR measurement of the thus-obtained intermediate (a) are as follows. $^1$H-NMR (300 MHz, CDCl$_3$): 7.96 (s, 1H), 4.15 (s, 3H), 3.81 (s, 3H)

(2) Synthesis of Intermediate (b)

150 ml of isopropanol is added to 7.4 ml (141 mmol) of methylhydrazine, followed by cooling to 15° C. (internal temperature). After gradually adding 7.0 g (49.6 mmol) of the intermediate (a) to this solution, the resulting mixture is heated to 50° C. and stirred for 1 hour and 40 minutes. This reaction solution is concentrated under reduced pressure, and is then subjected to purification by silica gel column chromatography to obtain 10.5 g (white powder; yield: 50%) of the intermediate (b). Results of NMR measurement of the thus-obtained intermediate (b) are as follows. $^1$H-NMR (300 MHz, CDCl$_3$): 7.60 (s, 1H), 4.95 (brs, 2H), 3.80 (s, 3H), 3.60 (s, 3H)

(3) Synthesis of Intermediate (c)

136 mL of water is added to 1.1 L of methanol, and 182 g (2.17 mol) of sodium hydrogencarbonate is added thereto, followed by stirring at room temperature. To the resulting mixture is added 200 g (1.08 mol) of cyanuric chloride by portions. After completion of the addition, the internal temperature is increased to 30° C. After stirring for 30 minutes at the same temperature, 500 mL of water is added thereto, and a precipitated solid product is collected by filtration, spray washed with 500 mL of water and 300 mL of methanol, and dried to obtain 168 g (white powder; yield: 86.2%) of the intermediate (c). Results of NMR measurement of the thus-obtained intermediate (c) are as follows. $^1$H-NMR (300 MHz, CDCl$_3$): 4.14 (s, 3H)

(4) Synthesis of Intermediate (d)

673 mL of water is added to 363 mL (7.46 mol) of hydrazine monohydrate, and the resulting mixture is cooled to 10° C. (internal temperature) and, after gradually adding to this mixed solution 168 g (934 mmol) of the intermediate (e) (at an internal temperature of 20° C. or lower), the ice bath is removed, and the temperature of the reaction solution is allowed to increase to room temperature, followed by stirring for 30 minutes at the same temperature. Crystals precipitated from the reaction solution are collected by filtration, spray washed with 700 mL of water and 1 L of acetonitrile, and dried to obtain the intermediate (d) (white powder).

(5) Synthesis of Intermediate (e)

480 mL of ethylene glycol is added to a crudely purified product of the intermediate (d), and the mixture is stirred at room temperature. To this suspension is added 257 g (2.06 mol) of pivaloylacetonitrile, and the resulting mixture is heated till the internal temperature reaches 80° C. A 12N potassium hydroxide hydrochloric acid aqueous solution is added thereto to adjust the pH to 3 and the resulting mixture is heated till the internal temperature reaches 80° C., followed by stirring for 3 hours. After completion of the reaction, the reaction solution is cooled with ice to an internal temperature of 8° C., and the precipitated crystals are collected by filtration, spray washed with water, and subjected to purification by silica gel chromatography to obtain 105 g (white powder; yield: 29.2% through two steps). Results of NMR measurement of the thus-obtained intermediate (e) are as follows. $^1$H-NMR (300 MHz, d-DMSO): 7.00 (s, 4H), 5.35 (s, 2H), 4.05 (s, 3H), 5.35 (s, 2H), 1.22 (s, 18H)

(6) Synthesis of α-Type Crystal Form Azo Pigment (I)

A mixed solution of 125 mL of acetic acid and 24 mL of sulfuric acid is cooled with ice to an internal temperature of 3° C. 26.4 g of nitrosylsulfuric acid is added thereto at the same temperature and, subsequently, 11.6 g of the intermediate (b) is added thereto by portions at the same temperature to dissolve. After stirring for 1 hour at the same temperature, 1.2 g of urea is added thereto by portions at the same temperature, followed by stirring for 15 minutes at the same temperature to obtain a diazonium salt solution. Separately, 11.0 g of the intermediate (e) is completely dissolved in 405 mL of methanol, and cooled with ice to an internal temperature of –3° C. The above-described diazonium salt solution is added thereto by portions so that the internal temperature becomes 3° C. or lower and, after completion of the addition, the reaction solution is stirred for 2 hours. The ice bath is removed, and the reaction solution is stirred at room temperature for 10 minutes. Precipitated crystals are collected by filtration, spray washed with 150 mL of methanol, then further spray washed with 100 mL of water. Crystals thus-obtained are suspended in 750 mL of water without drying, and a 8N potassium hydroxide aqueous solution is added thereto to adjust the pH to 5.7. After stirring at room temperature for 20 minutes, resulting crystals are collected by filtration, sufficiently spray washed with water, and then spray washed with 80 mL of methanol. The thus-obtained crystals are dried at room temperature for 12 hours.

The thus-obtained crystals are suspended in a mixed solution of 180 mL of dimethylacetamide and 180 mL of water, and then the internal temperature is raised to an internal temperature of 85° C., followed by stirring at the same temperature for 2 hours. Thereafter, the resulting crystals are collected by hot filtration and suspended in 300 mL of methanol, and the suspension is stirred at room temperature for 30 minutes. The resulting crystals are collected by filtration, and dried at room temperature for 5 hours to obtain 19.5 g of the α-type crystal form azo pigment (1) having the crystal form of the invention and represented by formula (1). Yield: 90.3%.

Visual observation of the thus-obtained α-type crystal form azo pigment (1) under a transmission microscope (manufactured by JEOL Ltd.; JEM-10 electron microscope) reveals that the length of the long axis of primary particles is about 150 nm.

When X-ray diffraction of the α-type crystal form azo pigment (1) is measured under the aforesaid conditions, characteristic X-ray peaks are shown at Bragg angles (2θ±0.2°) of 7.2° and 25.9.

The X-ray diffraction pattern with characteristic Cu Kα line is shown in FIG. 1

Synthesis Example 2

Synthesis of an Azo Pigment Composition Containing β-Type Crystal Form as a Major Component 10 g of the azo pigment (1) obtained in the foregoing Synthesis Example 1 is suspended in 100 mL of chloroform, and then the suspension is stirred for 30 minutes under reflux. Thereafter, the suspension is cooled to an internal temperature of 55° C. room temperature, followed by dropwise adding thereto 100 mL of methanol to cause precipitation. Subsequently, the mixture is stirred for 30 minutes at the same temperature, and then cooled to room temperature over 2 hours. The resulting crystals are collected by filtration, washed with methanol, and dried at 50° C. for 10 hours to obtain 8.8 g of the azo pigment having the β-type crystal form of the invention and represented by formula (1). Yield: 88.0%. Particle size of the thus-obtained azo pigment=ca. 10 μm (measured by using a transmission microscope, JEM-1010 electron microscope, manufactured by JEOL Ltd.)

Figure 2:
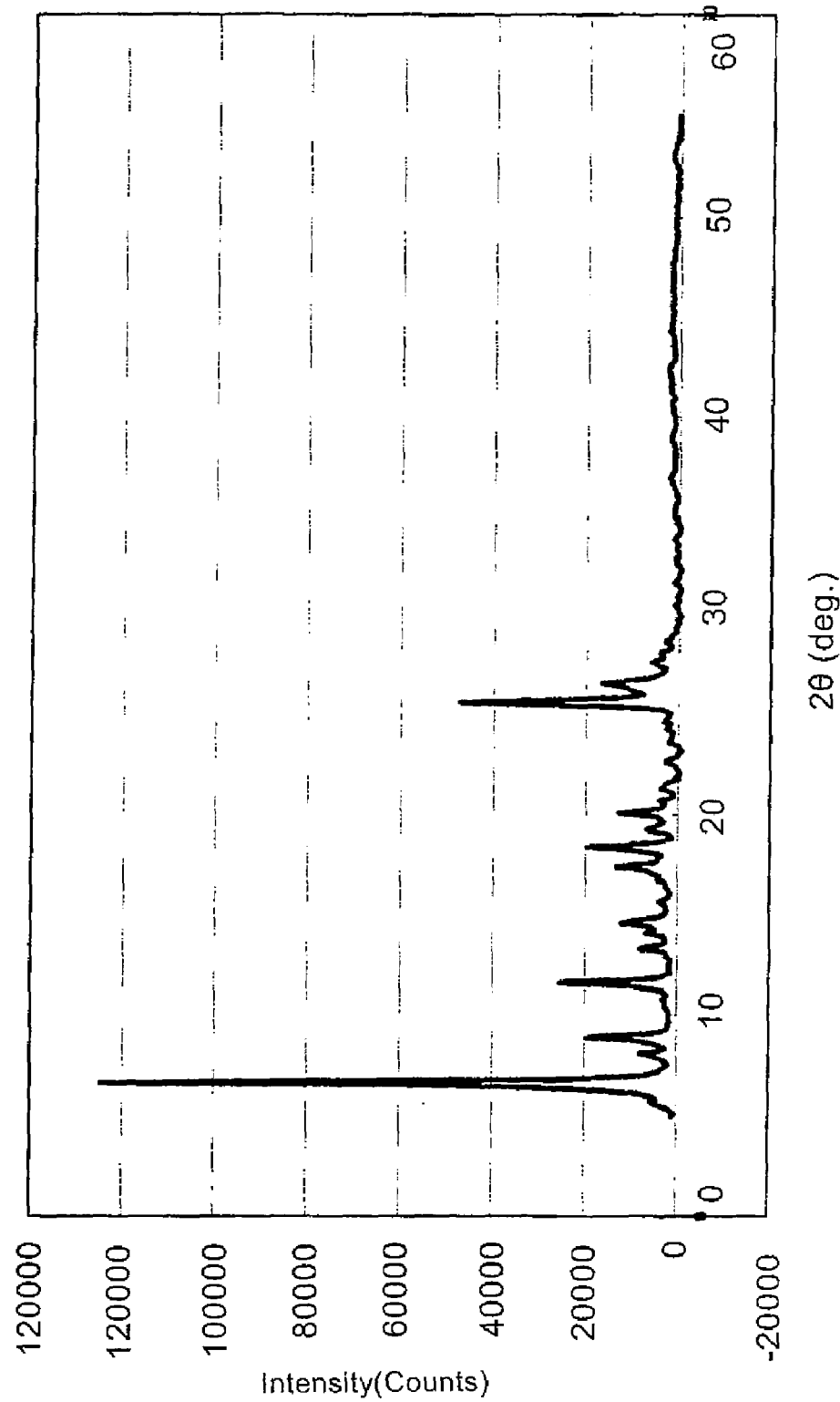
FIG. 2 is an X-ray diffraction pattern of an azo pigment (2) synthesized according to Synthesis Example 2.

The azo pigment composition is found to be an azo pigment composition (β-type crystal form azo pigment composition 2) which contains as a major component a β-type crystal form azo pigment having characteristic X-ray peaks at Bragg angles (2θ±0.2°) of 6.6°, 8.9°, 11.7°, 18.4°, 25.7°, and 26.7 shown in the X-ray diffraction pattern with characteristic Cu Kα line as shown in FIG. 2 or a tautomer thereof.

Example 11

Preparation of Pigment Dispersion 1

2.5 parts of the α-type crystal form azo pigment composition (1) synthesized in Synthesis Example 1, 0.5 part of sodium oleate, 5 parts of glycerin, and 42 parts of water are mixed with each other, followed by dispersing for 2 hours at a speed of 300 rotations per minute using a planetary ball mill containing 100 parts of zirconia beads of 0.1 mm in diameter. After completion of the dispersing procedure, the zirconia beads are removed to obtain a yellow pigment dispersion 1 (volume-average particle size: My=ca. 65 nm; measured by using Nanotrac 150 (UPA-EX150 manufactured by Nikkiso Co., Ltd.).

Example 12

Preparation of Pigment Dispersion 2

2.25 parts of the α-type crystal form azo pigment composition (1) synthesized in Synthesis Example 1, 0.25 part of the β-type crystal form azo pigment composition (2) synthesized in Synthesis Example 2, 0.5 part of sodium oleate, 5 parts of glycerin, and 42 parts of water are mixed with each other, followed by dispersing for 3 hours at a speed of 300 rotations per minute using a planetary ball mill containing 100 parts of zirconia beads of 0.1 mm in diameter. After completion of the dispersing procedure, the zirconia beads are removed to obtain a yellow pigment dispersion 2 (volume-average particle size: My=ca. 68 nm; measured by using Nanotrac 150 (UPA-EX150 manufactured by Nikkiso Co., Ltd.).

Example 13

Preparation of Pigment Dispersion 3

2.0 parts of the α-type crystal form azo pigment composition (1) synthesized in Synthesis Example 1, 0.5 part of the β-type crystal form azo pigment composition (2) synthesized in Synthesis Example 2, 0.5 part of sodium oleate, 5 parts of glycerin, and 42 parts of water are mixed with each other, followed by dispersing for 3 hours at a speed of 300 rotations per minute using a planetary ball mill containing 100 parts of zirconia beads of 0.1 mm in diameter. After completion of the dispersing procedure, the zirconia beads are removed to obtain a yellow pigment dispersion 3 (volume-average particle size: My=ca. 70 nm; measured by using Nanotrac 150 (UPA-EX150 manufactured by Nikkiso Co., Ltd.).

Example 14

Preparation of Pigment Dispersion 4

1.5 parts of the α-type crystal form azo pigment composition (1) synthesized in Synthesis Example 1, 1.0 part of the β-type crystal form azo pigment composition (2) synthesized in Synthesis Example 2, 0.5 part of sodium oleate, 5 parts of glycerin, and 42 parts of water are mixed with each other, followed by dispersing for 3 hours at a speed of 300 rotations per minute using a planetary ball mill containing 100 parts of zirconia beads of 0.1 mm in diameter. After completion of the dispersing procedure, the zirconia beads are removed to obtain a yellow pigment dispersion 4 (volume-average particle size: Mv=ca. 72 nm; measured by using Nanotrac 150 (UPA-EX150 manufactured by Nikkiso Co., Ltd.).

Example 15

Preparation of Pigment Dispersion 5

1.25 parts of the α-type crystal form azo pigment composition (1) synthesized in Synthesis Example 1, 1.25 part of the β-type crystal form azo pigment composition (2) synthesized in Synthesis Example 2, 0.5 part of sodium oleate, 5 parts of glycerin, and 42 parts of water are mixed with each other, followed by dispersing for 3 hours at a speed of 300 rotations per minute using a planetary ball mill containing 100 parts of zirconia beads of 0.1 mm in diameter. After completion of the dispersing procedure, the zirconia beads are removed to obtain a yellow pigment dispersion 5 (volume-average particle size: Mv=ca. 73 nm; measured by using Nanotrac 150 (UPA-EX150 manufactured by Nikkiso Co., Ltd.).

Comparative Example 1

Preparation of Comparative Pigment Dispersion 1

A yellow comparative pigment dispersion 1 (volume-average particle size: Mv≈118 nm measured by using Nanotrac 150 (UPA-EX150 manufactured by Nikkiso Co., Ltd.)) is obtained in the same manner as in Example 1 except for using C.I. Pigment Yellow 74 (Iralite YELLOW GO manufactured by Ciba Specialty Chemicals) in place of the α-type crystal form azo pigment composition (1).

Comparative Example 2

Preparation of Comparative Pigment Dispersion 2

A yellow comparative pigment dispersion 2 (volume-average particle size: Mv≈128 nm measured by using Nanotrac 150 (UPA-EX150 manufactured by Nikkiso Co., Ltd.)) is obtained in the same manner as in Example 1 except for using C.I. Pigment Yellow 155 (INKJET YELLOW 4G VP2532 manufactured by Clariant Co.) in place of the α-type crystal form azo pigment composition (1).

Comparative Example 2

Preparation of Comparative Pigment Dispersion 3

When the same procedures as in Example 1 are conducted except for using a compound (DYE-1) represented by the following formula (A) in place of the α-type crystal form azo pigment composition (1), the compound is dissolved, with no dispersion being obtained.

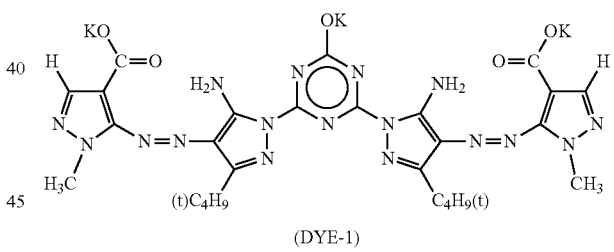

(DYE-1)

<Dispersibility>

2.5 parts of a pigment, 0.5 part of sodium oleate, 5 parts of glycerin, and 42 parts of water are mixed with each other, followed by dispersing for 2 hours at a speed of 300 rotations per minute using a planetary ball mill containing 100 parts of zirconia beads of 0.1 mm in diameter. After this dispersion, the pigment dispersions 1 to 5, comparative pigment dispersions 1 and 2, and comparative dispersion 3 are evaluated according to the following criteria: a sample found to contain coarse particles of 100 nm or larger is ranked B, a sample which fails to form a dispersion is ranked C, and a sample found to scarcely contain the coarse particles is ranked A. The results are shown in Table 1.

<Dispersion Stability>

The pigment dispersions obtained in the foregoing Examples 11 to 15 and in Comparative Examples 1 and 2 are allowed to stand at room temperature for 4 weeks. Then, samples which are visually found to form a precipitate are ranked B, and samples which are visually found to form no precipitate are ranked A.

<Evaluation of Hue>

Hue is evaluated according to the following criteria: samples of the above-obtained coated products which are less greenish and have large vividness in terms of chromaticity when viewed with the eye are ranked A (good); samples which are greenish or have less vividness are ranked B; and samples which are greenish and have less vividness are ranked C (bad). The results are shown in Table 1.

<Evaluation of Tinctorial Strength>

Each of the pigment dispersions obtained in the foregoing Examples 11 to 15 and Comparative Examples 1 and 2 is coated on Epson Photo Matte Paper using a No. 3 bar coater. Image density of each of the thus-obtained coated products is measured by means of a reflection densitometer (X-Rite 938; manufactured by X-Rite Co.). "Tinctorial strength (OD: Optical Density)" is evaluated according to the following criteria: samples showing an OD of 1.4 or more are ranked A; samples showing an OD of 1.2 or more and less than 1.4 are ranked B, and samples showing an OD less than 1.2 are ranked C. The results are shown in Table 1.

<Evaluation of Light Fastness>

The coated products of 1.0 in image density used in evaluation of hue are prepared and irradiated for 35 days with a xenon light (99,000 lux; in the presence of a TAC filter) using a fadeometer, and image density thereof is measured before and after irradiation with the xenon light. The pigment dispersions 1 to 5 and the comparative pigment dispersions 1 and 2 are evaluated in terms of colorant residual ratio [(density after irradiation/density before irradiation)×100%] according to the following criteria: samples with a colorant residual ratio of 80% or more are ranked A; samples with a colorant residual ratio of 60% or more and less than 90% are ranked B; and samples with a colorant residual ratio of less than 60% are ranked C. The results are shown in Table 1.

<Evaluation of Ozone Gas Fastness>

The coated products of 1.0 in image density used in evaluation of hue are prepared and exposed to an ozone gas for 28 days under the conditions of 5.0 ppm in ozone density, 25° C. in temperature, and 50% in humidity, and the image density of each sample is measured before and after exposure to the ozone gas by means of a reflection densitometer. The pigment dispersions 1 to 5 and the comparative pigment dispersion 1 and 2 are evaluated according to the following criteria: samples which show a colorant residual ratio [(density after exposure/density before exposure)×100%] of 80% or more are ranked A; samples with a colorant residual ratio of 70% or more are ranked B; and samples with a colorant residual ratio of less than 70% are ranked C. The results are shown in Table 1.

TABLE 1

| | Colorant Pigment composition | Volume-average Particle Size | Dispersibility | Dispersion Stability | Hue | Tinctorial Strength | Light Fastness | Ozone Gas Fastness |
| --- | --- | --- | --- | --- | --- | --- | --- | --- |
| Example 11 | α-type crystal form | 65 nm | A | A | A | A | A | A |
| Example 12 | α-form/β-form = 9/1 | 68 nm | A | A | A | AA | A | A |
| Example 13 | α-form/β-form = 8/2 | 70 nm | A | A | A | AA | AA | AA |
| Example 14 | α-form/β-form = 6/4 | 72 nm | A | A | B | AA | AA | AA |
| Example 15 | α-form/β-form = 5/5 | 73 nm | A | A | B | AA | AA | AA |
| Comparative Example 1 | PY-74 | 118 nm | B | A | B | A | C | B |
| Comparative Example 2 | PY-155 | 128 nm | B | A | C | C | B | B |
| Comparative Example 3 | DYE-1 | No dispersion is formed. | DissolvEd | — | — | — | — | — |

It is seen from the results that the pigment dispersion using the azo pigment composition of the invention is easily dispersible and has good stability. Further, a coloring composition containing the pigment dispersion of the invention is found to show excellent hue as yellow, high tinctorial strength, and excellent light fastness and ozone gas fastness.

Accordingly, the pigment-dispersed coloring composition containing the azo pigment composition of the invention can preferably be used in an ink for printing such as inkjet printing, a color toner for electro-photography, a color filter to be used for displays such as LCD and PDP, and photographing devices such as CCD, a paint, and in colored plastics.

INDUSTRIAL APPLICABILITY

According to the present invention, there is provided an azo pigment showing excellent coloring characteristics such as tinctorial strength and hue and showing excellent dispersibility and dispersion stability. A pigment dispersion showing excellent coloring characteristics and showing excellent dispersibility and dispersion stability can be obtained by dispersing the pigment of the invention in various media. The pigment dispersion can be used as a coloring material excellent in light fastness in, for example, an ink for printing such as inkjet printing, a color toner for electro-photography, a color filter to be used for displays such as LCD and PDP, and photographing devices such as CCD, a paint, and in colored plastics.

Although the invention has been described in detail and by reference to specific embodiments, it is apparent to those skilled in the art that it is possible to add various alterations and modifications insofar as the alterations and modifications do not deviate from the spirit and the scope of the invention.

This application is based on a Japanese patent application filed on Mar. 7, 2008 (Japanese Patent Application No. 2008-58711), a Japanese patent application filed on Jun. 27, 2008 (Japanese Patent Application No. 2008-169182), and a Japanese patent application filed on Dec. 9, 2008 (Japanese Patent Application No. 2008-313754), and the contents thereof are incorporated herein by reference.

The invention claimed is:

1. An azo pigment composition comprising at least one azo pigment represented by the following formula (1) and having characteristic peaks at Bragg angles($2\theta\pm0.2°$) of 7.2° and 25.9° in X-ray diffraction with the characteristic Cu Kα line, or a tautomer thereof:

(1):

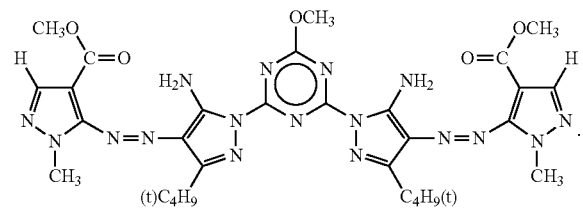

2. The azo pigment composition according to claim 1, which further comprises an azo pigment represented by the formula (1) and in a crystal form having characteristic peaks at Bragg angles ($2\theta\pm0.2°$) of 6.6°, 8.9°, 11.7°, 18.4°, 25.7°, and 26.7° in X-ray diffraction with the characteristic Cu Kα line, or a tautomer thereof in a content of from 0 to 50% by weight.

3. The azo pigment composition according to claim 2, wherein the content of the azo pigment represented by the formula (1) and in the crystal form having characteristic peaks at Bragg angles ($2\theta\pm0.2°$) of 6.6°, 8.9°, 11.7°, 18.4°, 25.7°, and 26.7° in X-ray diffraction with the characteristic Cu Kα line, or the tautomer thereof is from 0 to 20% by weight.

4. The azo pigment composition according to claim 2, wherein the content of the azo pigment represented by the formula (1) and in the crystal form having characteristic peaks at Bragg angles ($2\theta\pm0.2°$) of 6.6°, 8.9°, 11.7°, 18.4°, 25.7°, and 26.7° in X-ray diffraction with the characteristic Cu Kα line, or the tautomer thereof is from 0 to 10% by weight.

5. A process for producing an azo pigment composition comprising at least one azo pigment represented by the formula (1) and having characteristic peaks at Bragg angles ($2\theta\pm0.2°$) of 7.2° and 25.9° in X-ray diffraction with the characteristic Cu Kα line, or a tautomer thereof, the process comprising a step of conducting a diazo coupling reaction between a diazonium salt derived from a heterocyclic amine represented by the formula (2) and a compound represented by the formula (3):

(2):

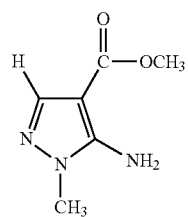

(3):

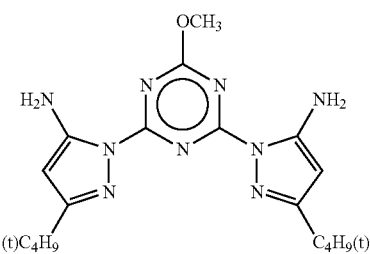

(1):

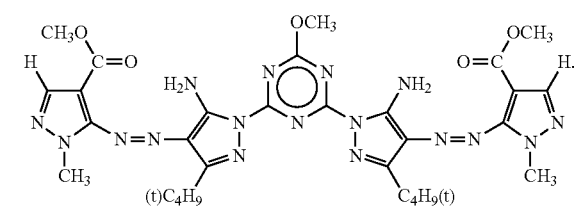

6. The production process according to claim 5, which further comprises a step of conducting after-treatment.

7. An azo pigment composition comprising at least one azo pigment represented by the formula (1) and having characteristic peaks at Bragg angles ($2\theta\pm0.2°$) of 7.2° and 25.9° in X-ray diffraction with the characteristic Cu Kα line, or a tautomer thereof, the azo pigment or tautomer thereof being produced by a production process of claim 5.

(1):

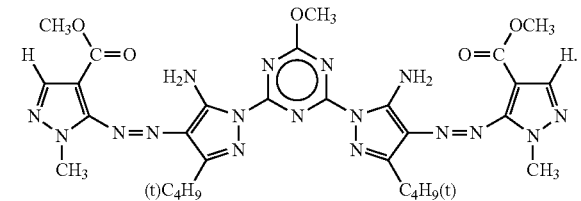

8. A pigment dispersion comprising the azo pigment composition described in claim 1.

9. The pigment dispersion according to claim 8, wherein the azo pigment contained in the azo pigment composition has a volume-average particle size of from 0.01 μm to 0.2 μm.

10. A coloring composition comprising as a colorant the azo pigment composition described in claim 1.

11. An ink for inkjet recording, comprising as a colorant an azo pigment composition described in claim 1.

* * * * *